United States Patent [19]
Efange et al.

[11] Patent Number: 5,948,807
[45] Date of Patent: Sep. 7, 1999

[54] SPIROINDANAMINES AND SPIROINDANIMIDES

[75] Inventors: S. Mbua Ngale Efange, Plymouth, Minn.; Deborah Carmen Mash, North Bay Village, Fla.

[73] Assignee: Regents of the University of Minnesota, Minneapolis, Minn.

[21] Appl. No.: 08/922,827

[22] Filed: Sep. 3, 1997

[51] Int. Cl.$^6$ ............ A61K 31/40; A61K 31/405; C07D 209/96; C07D 487/10
[52] U.S. Cl. ............ 514/409; 548/410; 548/411
[58] Field of Search ............ 514/409; 548/410, 548/411

[56] References Cited

U.S. PATENT DOCUMENTS 4,925,841  5/1990  Borenstein et al. .............. 514/235.5

FOREIGN PATENT DOCUMENTS

| | | | |
|---|---|---|---|
| 2150797 | 8/1972 | France | A61K 27/00 |
| 2241027 | 8/1972 | Germany | C07D 27/04 |
| 556835 | 8/1971 | Switzerland | C07D 27/04 |
| 96/11934 | 4/1996 | WIPO | C07D 491/107 |

OTHER PUBLICATIONS

Abou–Gharbia, M.A., et al., "Synthesis of Spirofluorenes of Biological Interest", *J. of Pharma. Sci.*, 67, 953–956, (1978).

Abou–Enein, M.N., et al., "1, 3–Substituted 2, 5–Pyrrolidinediones as Antiinflammatory Agents", *Pharmaceutica Acta Helvetiae*, 55 (2), 50–53, (1980).

Allen, R.C., et al., "Synthesis of Spiro[isobenzofuran–1 (3H), 4'–piperidines] as potential centralnervous system agents. 4. Central Nervous System Depressants", *J. of Med. Chem.*, 21 (11), 1149–1154, (1978).

Bauer, V.J., et al., "Synthesis of Spiro[isobenzofuran–1 (3H), 4'–piperidines] as potential central nervous system agents", *J. of Med. Chem.*, 19 (11), 1315–1324, (1976).

Borenstein, M.R., et al., "Anticonvulsant activity of indanylspirosuccinimide Mannich bases", *J. of Pharma. Sci.*, 76 (4), 300–302, (1987).

Borenstein, M.R., et al., "Synthesis of Spiroimides of Pharmacologic Interest", *Heterocycles*, 22 (11), 2433–2438, (1984).

Crooks, P.A., et al., "Synthesis and analgesic properties ofsome conformationally restricted analogues of profadol", *J. of Med. Chem.*, 23 (6), 679–682, (1980).

(List continued on next page.)

*Primary Examiner*—Robert W. Ramsuer
*Assistant Examiner*—Jane C. Oswecki
*Attorney, Agent, or Firm*—Schwegman, Lundberg, Woessner & Kluth, P.A.

[57] ABSTRACT

Compounds of formula I:

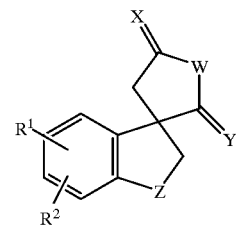

(I)

wherein $R^1$, $R^2$, W, X, Y and Z have any of the values defined in the specification, and their pharmaceutically acceptable salts, are inhibitors of monoamine re-uptake and are useful for treating diseases in mammals wherein insufficient synaptic levels of monoamine are implicated. Also disclosed are pharmaceutical compositions, processes for preparing compounds of formula I, and intermediates useful for the synthesis of compounds of formula I.

20 Claims, 4 Drawing Sheets

OTHER PUBLICATIONS

Crooks, P.A., et al., "Synthesis of spiro[tetralin–2,2'–pyrrolidine] and Spiro[indan–2,2–'pyrrolidine] derivatives as potential analgesics", *J. of Med. Chem.,* 21 (6), 585–587, (1978).

Crooks, P.A., et al., "The synthesis and analgesic activities of some spiro[indan–1,3'–pyrrolidine] derivatives designed as rigid analogs of profadol", *J. of Pharma. Sci.,* 71 (3), 291–294, (1982).

Klioze, S.S., et al., "Spiro[isobenzofuran–1 (3H) , 4'–piperidines]. 3. Diuretic and antihypertensive properties of compounds containing a sulfur attached to nitrogen", *J. of Med. Chem.,* 21 (4), 400–403, (1978).

Klioze, S.S., et al., "Synthesis of Spiro[isbenzofuran–1 (3H), 4'–piperidines] as potential central nervous system agents. 2. Compounds containing a heteroatom attached to nitrogen", *J. of Med. Chem.,* 20 (4), 610–612, (1977).

Nagai, Y., et al., "Studies on Psychotropic agents. VI. Synthesis of 1'–methylspiro[6–fluoroindan–1,3'–pyrrolidine]–3–one and related compounds", *Chem. Pharma. Bull.,* 28 (5), 1387–1393, (1980).

Paul, S.M., et al., "Demonstration of specific "high affinity" binding sites for [3H] imipramine on human platelets", *Life Sci.,* 26 (12), 953–959, (1980).

Pletscher, A., "Platelets as Models for Monoaminergic Neurons", *Essays in Neurochemistry and Neuropharmacology, J. Wiley & Sons,* vol. 3, M.B.H. Youdim et al., eds., 49–101, (1978).

Sandberg, R., et al., "N–aminoalkylsuccinimides as local anaesthetics", *Acta Pharm. Suec.,* 17, 177–182, (1980).

Schildkraut, J.J., et al., "Biogenic Amines and Emotion", *Science,* 156 (771), 21–37, (1967).

Sommerville, R., et al., "Synthesis and Pharmacological Evaluation of Aromatic Dihydroxylated spiro[indan–1, 3'–pyrrolidine] and spiro[indan–2,2'–pyrrolidine] Derivatives", *J. of Pharm. Sci.,* 74 (5), 553–555 (1985).

Sotiropoulou, E., et al., "Synthesis and pharamcochemistry of some new aminoketones wih local anaesthetic activity", *Arzneimittel–Forschung,* 44 (6), 702–706, (1994).

Strasser, v., et al., "Chemie des 2–Aminospiro [indan–1, 3'–pyrrolidin]–systems", *Helvetica Chimica Acta,* 62 (8), 2860–2866, (1979).

Van Praag, H.M., "Neurotransmitters and CNS Disease", *The Lancet,* 2 (8310), 1259–1264, (1982).

a: NaBH₄, MeOH, r.t.; b: SOCl₂, pyridine, 0°C to r.t.; c: NaCN, DMF, KI (cat.), 70 °C;
d: BrCH₂CN, LDA, THF, -78° to -60 °C to r.t.; e: 78% H₂SO₄-HOAc (w/v), 125 °C;
f: BH₃·THF, reflux; g: 50% HBr-HOAc, reflux; h: cyclopropylmethyl bromide, K₂CO₃, DMF, r.t.

a: ethyl cyanoacetate, pyrrolidine, HOAc, benzene, reflux (-$H_2O$);
b: KCN, aq. EtOH, 60 °C; c: 78% $H2SO4$ - HOAc (w/v), 125 °C.
d: $BH_3$.THF, reflux.

SPIROINDANAMINES AND SPIROINDANIMIDES

GOVERNMENT SUPPORT

This invention was made with U.S. Government support under AG13621 awarded by the National Institutes of Health. The Government has certain rights in the invention.

BACKGROUND OF THE INVENTION

Chemical neurotransmission can be described as a cyclical phenomenon involving the following distinct events: 1) arrival of an action potential at the presynaptic terminal; 2) depolarization of the presynaptic membrane followed by release of neurotransmitter via storage or synaptic vesicles; 3) binding of neurotransmitter to receptors on the postsynaptic terminal resulting in propagation of the signal (by second messengers); 4) dissociation of neurotransmitter from the receptors (to terminate the signal); 5) and removal of the neurotransmitter from the synaptic cleft. Since the neurotransmitter binds reversibly to the receptor, termination of the signal is critically dependent on the concentration of neurotransmitter within the synaptic cleft. Consequently, modulation of synaptic levels of neurotransmitter can have profound physiological significance. Not surprisingly, synaptic levels of most neurotransmitters in the brain are tightly regulated.

The levels of neurotransmitter in the synapse are controlled by two major mechanisms: re-uptake and metabolism. For the monoamines, re-uptake is mediated by transporters (dopamine transporter or DAT for dopamine, norepinephrine transporter or NET for norepinephrine and serotonin transporter or SERT for serotonin). Recent cloning experiments have revealed that these plasma membrane proteins contain twelve transmembrane domains and share considerable sequence homology. In spite of these similarities, the three monoamine transporters exhibit differences in sensitivity to inhibitors and substrate specificity.

Beginning with the discovery that tricyclic antidepressants inhibit the re-uptake of serotonin (reviewed in Pleschter, Essays in Neurochemistry, J. Wiley, 1978, p.49) and the subsequent demonstration of high-affinity binding sites for tricyclic antidepressants on platelets, and on rat and human brain (reviewed in Paul et al., Life Sci., 26, 953–959, 1980), advances in neuroscience continue to highlight the importance of neurotransporters in central nervous system function. For instance, recent experiments with knockout mice clearly demonstrate that the dopamine transporter, through its regulation of synaptic levels of this monoamine, plays a critical role in the rewarding effects of cocaine.

In addition, treatment of depression is largely based on the view that this disorder is associated with low synaptic levels of serotonin (van Praag, Lancet 8310, 1259–1264, 1982) or catecholamines (Schildkraut and Kety, Science 156, 21–30, 1967). Monoamines such as serotonin also play an important role in the control of mood, sexual function, appetite, craving and a number of other biological functions. Consequently, pharmacologic modulation of monoamine levels in the synaptic cleft presents a viable approach for the treatment of neurologic and neuropsychiatric disorders characterized by low synaptic levels of monoamine. Accordingly, inhibitors of monoamine re-uptake have been used for the treatment of neuropsychiatric disorders, including depression, obesity, sexual dysfunction, alcoholism, cocaine dependence (craving), bulimia, anorexia nervosa, attention deficit hyperactivity disorder, and obsessive-compulsive disorder.

Recently, the growing importance of neurotransporters has been further highlighted by the discovery that both the DAT and the SERT contain multiple binding sites for inhibitors. Since the different binding loci most likely mediate separate and distinct functions, compounds which discriminate between two sites on a given neurotransporter would be expected to display unique pharmacological profiles.

The realization that the aminoalkyl(aryl)isobenzofuran, fragment 14 (FIG. 2), is a recurring structural motif of the potent antidepressants 13 and talopram, prompted the design of a class of 3-arylspirophthalans represented by 15. In animals, certain of these compounds showed marked antidepressant activity (Bauer et al., J. Med. Chem., 19, 1315–1324, 1976; Klioze et al., J. Med. Chem., 20, 610–612, 1977), while others displayed depressant or neuroleptic activity (Allen et al., J. Med. Chem., 21, 1149–1154, 1978). A third group displayed antihypertensive and diuretic properties (Klioze and Novick, J. Med. Chem., 21, 400–403, 1978).

In their search for new analgesics, Crooks and Rosenberg (J. Med. Chem., 21, 585–587, 1978) synthesized derivatives of spiro[tetralin-2,2'-pyrrolidine] (16) and spiro[indan-2,2'-pyrrolidine] (17). Two compounds from the first group showed good analgesic activity, while some compounds from both groups displayed weak anti-depressant properties.

In a subsequent study involving derivatives of spiro[tetralin-1,3'-pyrrolidine] (18) (Crooks and Szyndler, J. Med. Chem. 23, 679–682, 1980), most compounds displayed little or no analgesic activity. Similar results were obtained for spiro[indan-1,3'-pyrrolidine], 19, and its derivatives (Crooks and Sommervile, J. Pharm. Sci., 71, 291–294, 1982). However, hydroxylated derivatives of 19 displayed weak dopamine antagonist (depressant) activity but no dopamine agonist activity (Sommervile et al., J. Pharm. Sci., 74, 553–555, 1985). Nagai et al. (Chem. Pharm. Bull., 28, 1387–1393, 1980) have also found that the spiro[indane-1, 3-pyrrolidine] 20 displays moderate central nervous system-depressing activity in rodents.

However, the butyrophenone-substituted compounds 21 display greater CNS depressant activity (Bastian et al., suppl. to Swiss patent #556,835; suppl. to French patent 2,150,797; also German patent 2,241,027). On the other hand, spiro compounds of type 28 are serotonin 5-HT$_{ID}$ antagonists (Wyman et al., PCT Int. Appl. WO 96 11,934). Strasser et al. (Helv. Chim. Acta 62, 2860–2868, 1979) also report the synthesis of spiroindanamide 22. However, no biological activity is reported for this compound or its derivatives.

Spiroindanimides of type 26 (Abou-Gharbia et al., J. Pharm. Sci. 67, 953–956, 1978; Borenstein et al., Heterocyles 22, 2433–2438, 1984) exhibit weak to moderate anticonvulsant activity in rodents (Borenstein and Doukas, J. Pharm. Sci. 76, 300–302,1987), and those of the type 25 display anti-inflammatory activity (Aboul-Enein et al., Pharm. Acta Helv. 55, 50–53,1980). Compounds of type 26 also display tranquilizing activity (New and Yevich, U.S. Pat. No. 83-531519). Other spiroindanimides of the type 27 (Sandberg et al., Acta Pharm. Suec. 17, 177–182, 1980) and 23, 24 (Sotiropoulou and Kourounakis, Arzneim.-Forch./Drug Res., 44, 702–706, 1994) exhibit local anesthetic properties. Viewed collectively, the foregoing suggests that the relationship between molecular structure and function is extremely complex.

Currently, there is a need for novel, potent, and selective agents to modulate synaptic neurotransmitter levels. Such agents would be useful for the treatment of neurologic and neuropsychiatric disorders, and as pharmacological tools for the further study of the physiological processes associated with monoamine neurotransmitters.

SUMMARY OF THE INVENTION

The invention provides compounds which are inhibitors of monoamine re-uptake. In particular, the invention provides compounds which are serotonin re-uptake inhibitors. According to the invention there is provided a compound of the invention which is a compound of formula I:

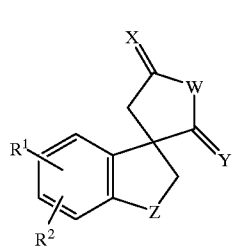

(I)

wherein

X and Y are each independently two hydrogens $(H)_2$, oxo, or thioxo;

$R^1$ and $R^2$ are each independently hydrogen, halo, hydroxy, cyano, $N(R_a)(R_b)$, $(C_1-C_6)$alkyl, $(C_1-C_6)$alkoxy, $(C_1-C_6)$alkanoyl, $(C_1-C_6)$alkanoyloxy, or $(C_3-C_6)$cycloalkyl; wherein $R_a$ and $R_b$ are each independently hydrogen, $(C_1-C_6)$alkyl, $(C_1-C_6)$alkanoyl, phenyl, benzyl, or phenethyl; or $R_a$ and $R_b$ together with the nitrogen to which they are attached are a 5–6 membered heterocyclic ring, i.e. a pyrrolidino, piperidino or morpholino ring;

W is —$N(R_c)$—, oxy or thio;

Z is —$N(R_d)$— or —$C(R_e)(R_f)$—;

$R_c$, $R_d$, $R_e$, and $R_f$ are each independently hydrogen, $(C_1-C_6)$alkyl, $(C_3-C_6)$cycloalkyl, aryl, heteroaryl, aryl $(C_1-C_6)$alkyl, heteroaryl$(C_1-C_6)$alkyl, $(C_1-C_6)$alkanoyl, arylcarbonyl, heteroarylcarbonyl, arylcarbonyl$(C_1-C_6)$alkyl, or heteroarylcarbonyl $(C_1-C_6)$alkyl, wherein any aryl or heteroaryl may optionally be substituted on carbon by 1, 2 or 3 U;

each U is independently halo, nitro, cyano, hydroxy, trifluoromethyl, trifluoromethoxy, $(C_1-C_6)$alkyl, $(C_3-C_6)$cycloalkyl, $(C_1-C_6)$alkoxy, $(C_1-C_6)$alkanoyl, $(C_2-C_6)$alkanoyloxy, $C(=O)OR_g$, $C(=O)NR_hR_i$, or $NR_jR_k$;

wherein any $(C_1-C_6)$alkyl, $(C_3-C_6)$cycloalkyl, or $(C_1-C_6)$ alkoxy in $R^1$, $R^2$, $R_c$, $R_d$, $R_e$, $R_f$, or U may optionally be substituted on carbon by 1, 2 or 3 V;

each V is independently halo, nitro, cyano, hydroxy, $(C_3-C_6)$cycloalkyl, $(C_1-C_6)$alkoxy, $(C_1-C_6)$alkanoyl, $(C_2-C_6)$alkanoyloxy, $C(=O)OR_m$, $C(=O)NR_nR_o$, $NR_pR_q$;

$R_h$, $R_i$, $R_m$, $R_n$, and $R_o$ are each independently hydrogen or $(C_1-C_6)$alkyl; and $R_j$, $R_k$, $R_p$, and $R_q$ are each independently hydrogen, $(C_1-C_6)$alkyl, $(C_1-C_6)$alkanoyl, phenyl, benzyl, or phenethyl; or $R_h$, and $R_i$, $R_j$ and $R_k$, $R_n$, and $R_o$, or $R_p$ and $R_q$ together with the nitrogen to which they are attached are a 5–6 membered heterocyclic ring, i.e. a pyrrolidino, piperidino or morpholino ring;

or a pharmaceutically acceptable salt thereof.

The invention also provides pharmaceutical compositions comprising a compound of the invention, processes for preparing compounds of the invention, novel intermediates useful for the synthesis of compounds of the invention (including the novel intermediates shown in FIGS. 3 or 4), and therapeutic methods comprising administering compounds of the invention.

DETAILED DESCRIPTION OF THE INVENTION

Figure 1:
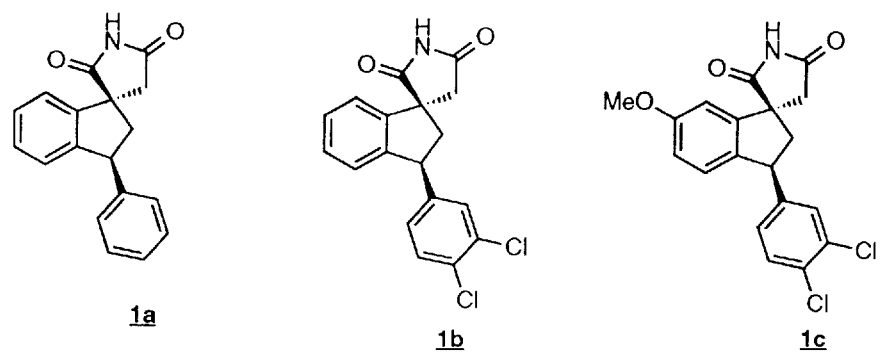
FIG. 1 shows compounds disclosed herein.
Figure 1:
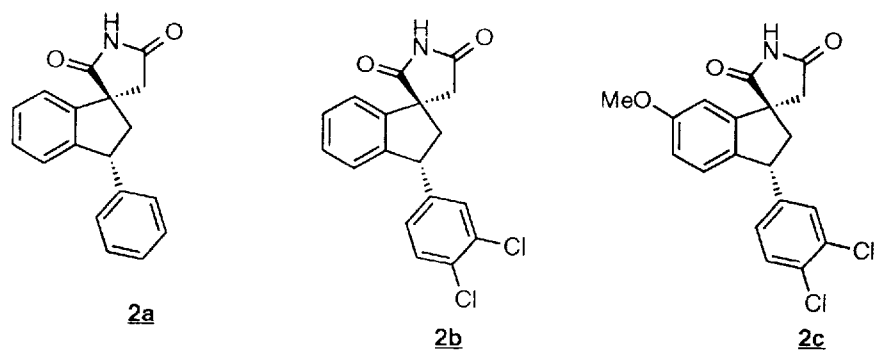
Figure 1:
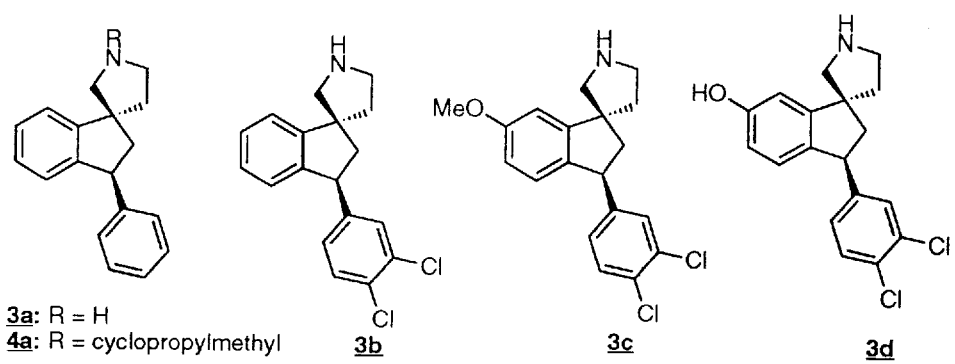
Figure 1:
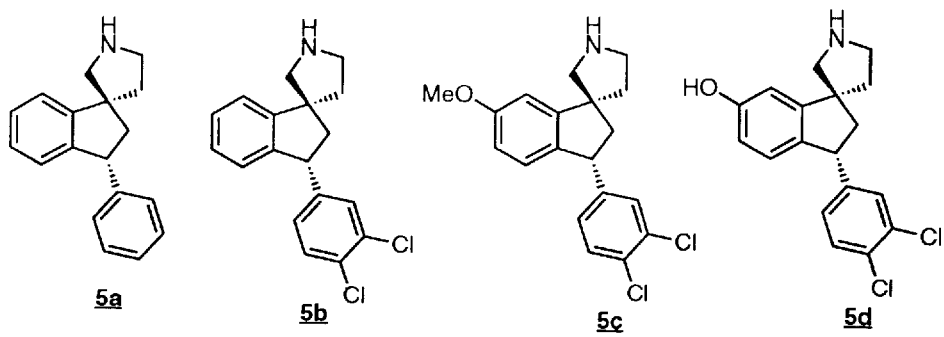
Figure 2:
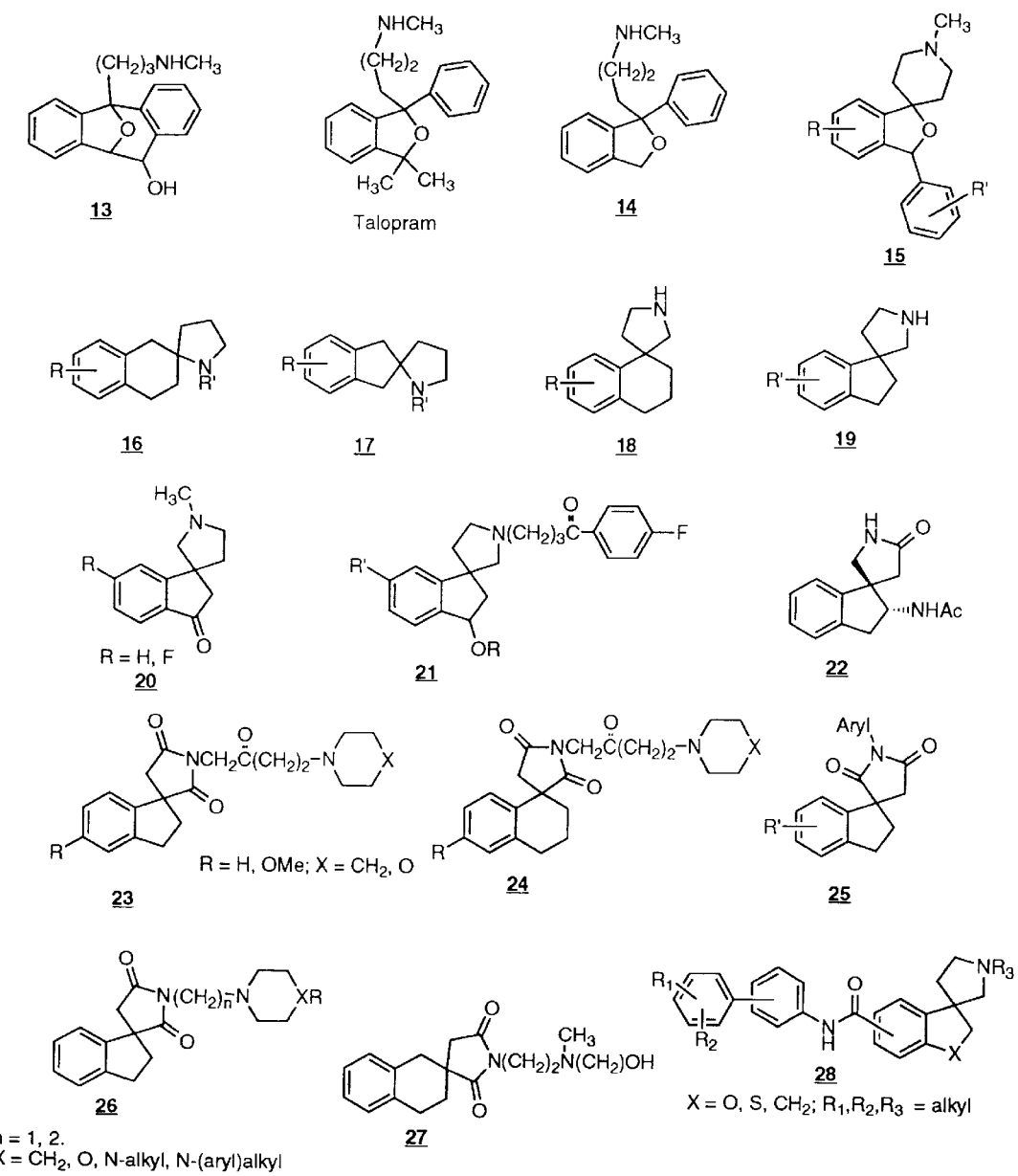
FIG. 2 shows prior art compounds.

The following definitions are used, unless otherwise described. Halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and $N(R_x)$ wherein $R_x$ is absent or is hydrogen, oxo, $(C_1-C_4)$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase) and how to determine the ability of a compound to inhibit monoamine re-uptake using the tests described herein, or using other tests which are well known in the art.

Specific and preferred values listed below for radicals, substituents, and ranges, are for illustration only; they do not exclude other defined values or other values within defined ranges for the radicals and substituents Specifically, $(C_1-C_6)$alkyl can be methyl, ethyl, propyl, isopropyl, butyl, isobutyl, sec-butyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexoxy; $(C_1-C_6)$alkanoyl can be acetyl, propanoyl or butanoyl; $(C_2-C_6)$alkanoyloxy can be acetoxy, ethylcarbonyloxy or propylcarbonyloxy; and $(C_3-C_6)$ cycloalkyl can be cyclopropyl, cyclobutyl, cyclopentyl or cyclohexyl. Aryl can be phenyl, indenyl, or naphthyl and heteroaryl can be furyl, imidazolyl, tetrazolyl, pyridyl, (or its N-oxide), thienyl, pyrimidinyl (or its N-oxide), indolyl, or quinolyl (or its N-oxide).

A specific group of compounds are compounds wherein X and Y are each two hydrogens.

A specific group of compounds are compounds wherein X and Y are each oxo.

A specific group of compounds are compounds wherein W is —N($R_c$)—.

A specific group of compounds are compounds wherein W is oxy or thio.

A specific group of compounds are compounds wherein Z is —N($R_d$)—.

A specific group of compounds are compounds wherein Z is —C($R_e$)($R_f$)—.

Preferably, $R^1$ is methoxy and $R^2$ is hydrogen.

Preferably, $R_c$ is hydrogen or cyclopropylmethyl.

Preferably, $R_d$ is phenyl or 3,4-dichlorophenyl.

Preferably, $R_e$ is hydrogen; and $R_f$ is phenyl or 3,4-dichlorophenyl.

Preferably, any ($C_1$–$C_6$)alkyl or ($C_1$–$C_6$)alkoxy in $R^1$, $R^2$, $R_c$, $R_d$, $R_e$, $R_f$, or U may optionally be substituted on carbon by 1 V.

A preferred group of compounds are compounds of formula I wherein X and Y are each independently two hydrogens or oxo; $R^1$ and $R^2$ are each independently hydrogen, hydroxy, or ($C_1$–$C_6$)alkoxy; W is —N($R_c$)—; $R_c$ is hydrogen, ($C_3$–$C_6$)cycloalkyl, or ($C_1$–$C_6$)alkyl optionally substituted with ($C_3$–$C_6$)cycloalkyl; Z is —C($R_e$)($R_f$)—; $R_e$ is hydrogen; $R_f$ is aryl, optionally substituted on carbon by 1, 2 or 3 U; each U is independently halo, hydroxy, trifluoromethoxy, ($C_1$–$C_6$)alkyl, ($C_3$–$C_6$)cycloalkyl, ($C_1$–$C_6$)alkoxy, or $NR_jR_k$; and $R_j$ and $R_k$ are each independently hydrogen or ($C_1$–$C_6$)alkyl; or a pharmaceutically acceptable salt thereof.

Processes for preparing compounds of formula I are provided as further embodiments of the invention and are illustrated by the following procedures in which the meanings of the generic radicals are as given above unless otherwise qualified. Compounds of formula I wherein X and Y are each oxo can be prepared from a corresponding compound of formula II:

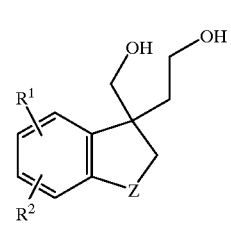

(II)

by treatment with acid. For example, suitable conditions for the conversion of a compound of formula II to a compound of the invention can be found at Example 1.

Compounds of formula I wherein X and Y are each two hydrogens can be prepared from a corresponding compound of formula I wherein X and Y are each oxo by reduction. Suitable conditions for such a reduction can be found at Example 3 and Example 10.

Compounds of formula I bearing an aromatic hydroxy substituent can be prepared from a corresponding compound of formula I bearing an aromatic methoxy substituent by hydrolysis. Suitable conditions for such a hydrolysis can be found at Example 4.

Compounds of formula I wherein W is —N($R_c$)— and $R_c$ is other than hydrogen can be prepared from a corresponding compound of formula I wherein $R_c$ is hydrogen by alkylation or acylation of the W nitrogen. Suitable conditions for such an alkylation can be found at Example 6.

Compounds of formula I wherein X and Y are each two hydrogens and W is oxy can be prepared from a corresponding diol of formula III

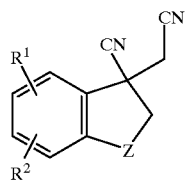

(III)

by dehydration.

A convenient intermediate for the preparation of compounds of the invention is a compound of formula II.

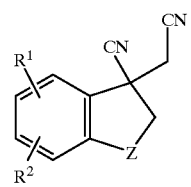

(II)

Figure 3:
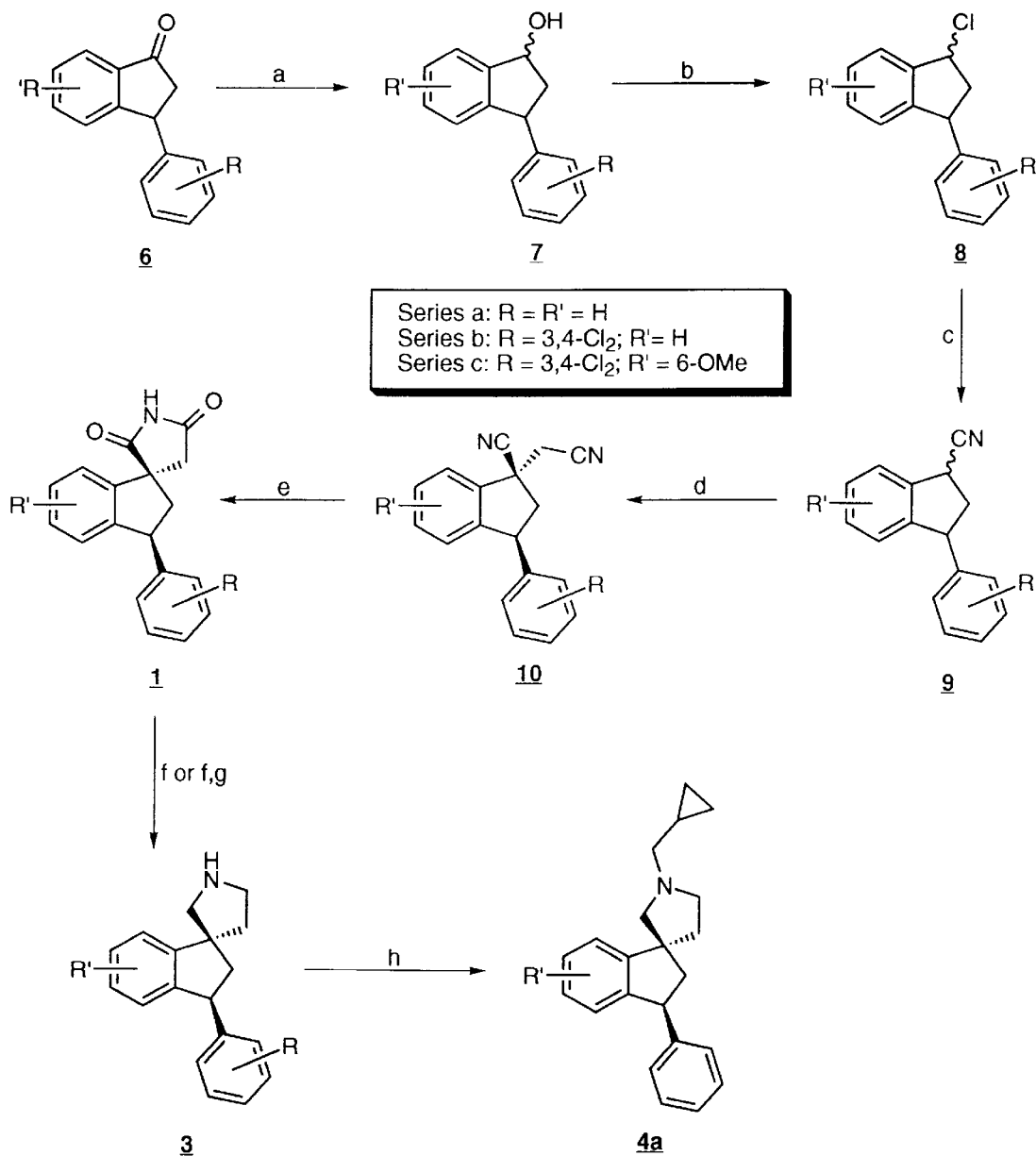
FIG. 3 illustrates the preparation of compounds of the invention.

An intermediate of formula II can be prepared as illustrated in FIG. 3. Indanone 6 can be reduced to the corresponding indanol 7 which can be converted to the benzylic chloride 8, for example, using thionyl chloride. Reaction of 8 with potassium cyanide followed by alkylation of the resulting mononitrile 9, for example with bromoacetonitrile, gives the dinitrile 10. This pathway provides almost exclusively the cis-spiro[indan-1,3'-pyrrolidine]-2',5'-diones as revealed by proton NMR, suggesting that under the conditions used for the alkylation of the mononitrile 9, the alkyl halide approaches from the less hindered face of the molecule.

Figure 4:
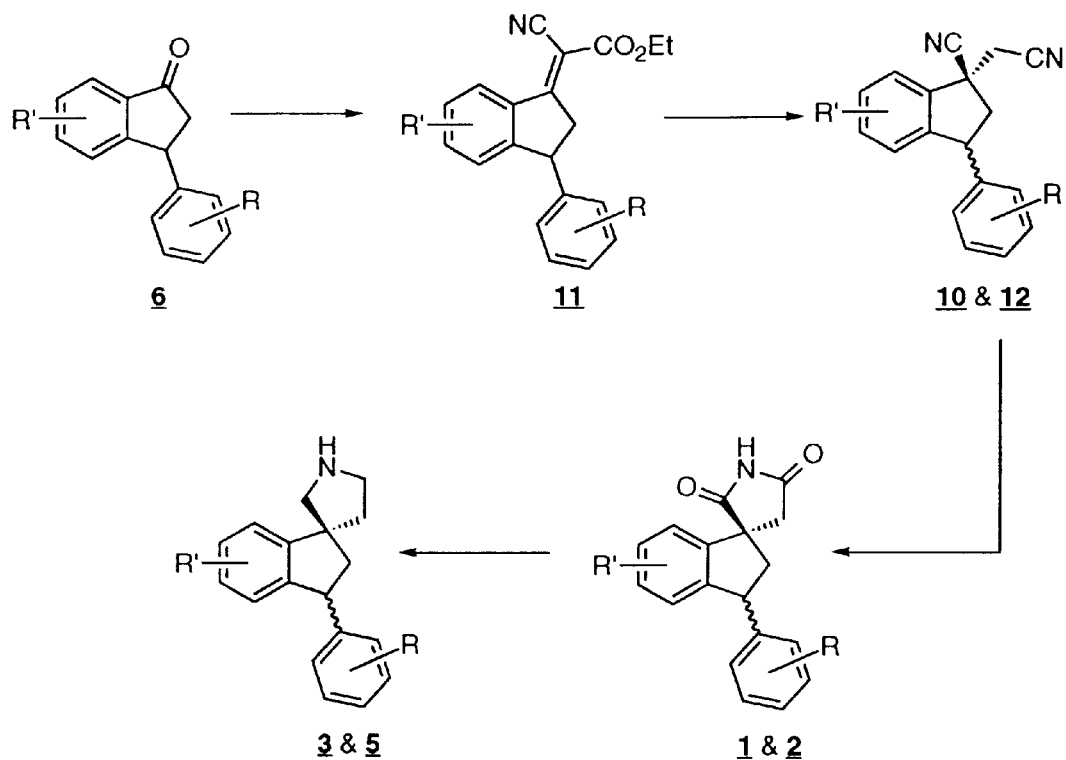
FIG. 4 illustrates the preparation of compounds of the invention.

An intermediate of formula II can also be prepared as illustrated in FIG. 4. Indanone 6 can be converted to the corresponding Claisen-Schmidt adduct 11 under standard conditions. Cyanide addition followed by decarboxylation gives a diastereomeric mixture of compounds 10 and 12, which can be converted to the corresponding spiro[indan-1,3'-pyrrolidin]-2',5'-diones using a procedure similar to that described at Example 8, or using a procedure similar to that described in Crooks and Sommerville, *J. Pharm. Sci.* 1982, 71, 291–294. In contrast to the pathway illustrated in FIG. 3, this route provides a 2:1 mixture of cis (1) and trans (2) isomers as revealed by proton NMR. Reduction with borane-THF provides the spiroindanamines 3 and 5 which can be separated by HPLC on silica gel (methanol-methylene chloride) or by fractional crystallization using a procedure similar to that described in Bogeso, *J. Med. Chem.*, 1983, 26, 935–947.

An intermediate of formula III can be prepared by hydrolysis of a corresponding dinitrile of formula II followed by esterification of the resulting diacid and subsequent reduction of the diester. Reagents and conditions suitable for carrying out these transformations are well known in the art.

It is noted that many the starting materials employed in the synthetic methods described above are commercially available or are reported in the scientific literature. For example, the intermediate 3-aryl-1-indanones 6b and 6c can be prepared as described in Bogeso, *J. Med. Chem.*, 1983, 26, 935–947; Bogeso et al., *J. Med. Chem.*, 1985, 28, 1817–1828.

It is also noted that it may be desirable to optionally use a protecting group during all or portions of the above described synthetic procedures. Such protecting groups and methods for their introduction and removal are well known in the art.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%. Single dosages for injection, infusion or ingestion will generally vary between 50–1500 mg, and may be administered, i.e., 1–3 times daily, to yield levels of about 0.5–50 mg/kg, for adults.

Accordingly, the invention includes a pharmaceutical composition comprising a compound of formula I as described hereinabove; or a pharmaceutically acceptable salt thereof, in combination with a pharmaceutically acceptable carrier.

The ability of a compound of the invention to inhibit monoamine re-uptake can be demonstrated using the pharmacological models described herein, or using other pharmacological models which are known in the art.

In Vitro Studies

Representative compounds of the invention were tested for binding at selected binding sites with the aid of radioligand binding techniques. All compounds were tested in racemic form. The spiroindanamines were tested as the hydrochlorides. SERT-1 refers to the cocaine binding site on the serotonin transporter, and SERT-2 refers to the paroxetine binding site on the same transporter. DAT is the dopamine transporter, and mu and kappa refer to the mu and kappa opioid receptors.

TABLE 1

Affinities ($IC_{50}$, $\mu M$) of Selected Compounds at Monoamine Transporters. (Radioligands are shown in parenthesis)

| TARGET | SERT-1 (RTI-55) | SERT-2 ([$^3$H]Paroxetine) | DAT ([$^3$H]WIN35,428) |
|---|---|---|---|
| 1a | 26.70 | >100 | NT |
| 1c | 0.25 | >100 | NT |
| 3a | 0.01 | 2.5 | 0.2 |
| 3c | 0.002 | 0.4 | 0.15 |
| 3d | 0.75 | 0.3 | 0.73 |
| 4a | 2.41 | 2.0 | 2.9 |

TABLE 2

Affinities ($IC_{50}$, $\mu M$) of Selected Compounds at Opioid Receptors. (Radioligands are shown in parenthesis)

| TARGET | Mu OPIOID ([$^{125}$I]DAMGO) | Kappa OPIOID ([$^3$H]U69593) |
|---|---|---|
| 1a | 100 | >100 |
| 1c | 100 | >100 |

TABLE 2-continued

Affinities ($IC_{50}$, $\mu M$) of Selected Compounds at Opioid Receptors. (Radioligands are shown in parenthesis)

| TARGET | Mu OPIOID ([$^{125}$I]DAMGO) | Kappa OPIOID ([$^3$H]U69593) |
|---|---|---|
| 3a | 0.5 | 10 |
| 3c | 5 | 80 |
| 3d | 2.9 | 1.52 |
| 4a | 0.98 | 1 |

Affinities of Reference compounds

For comparison, the following values are provided: Fluoxetine (SERT-1), 0.034 $\mu M$; Paroxetine (SERT-2), 0.001 $\mu M$; GBR12935 (DAT), 0.002 $\mu M$; U50488 (kappa), 0.003 $\mu M$; Naloxone (mu), 0.002 $\mu M$.

Binding at Monoamine Transporters

Compounds 3a and 3c displayed low nanomolar affinity for the high-affinity binding site of cocaine on the serotonin transporter (hereinafter referred to as SERT-1) and moderate to weak affinity at the low-affinity cocaine binding site (SERT-2) on this transporter. The affinity of these compounds for the serotonin transporter is comparable to or higher than that of other specific serotonin re-uptake inhibitors (SSRIs), such as citalopram, sertraline and fluoxetine, which are currently used as anti-depressants.

Although the nitrogen atom of the spiroindanimides is not basic, it is important to note that 1c displays higher affinity for SERT-2 than the basic spiroindanamines 3d and 4a. From this data it is reasonable to conclude: 1) that a basic nitrogen is not necessary for binding to SERT-2, and 2) that moderate- or high-affinity ligands for SERT-2 can be obtained by replacing the said nitrogen atom with another heteroatom, such as oxygen or sulfur. Accordingly, such compounds are also included as compounds of the invention.

Compounds of the invention have been shown to bind to the monoamine transporters DAT, SERT-1, and SERT-2. As a result the compounds may be useful for inhibiting monoamine re-uptake. Accordingly, the invention includes a therapeutic method for inhibiting re-uptake of a monoamine (for example dopamine, norepinephrine or serotonin) in a mammal such as a human, comprising administering to a mammal in need of such therapy, an effective amount of a compound of formula I, or a pharmaceutically acceptable salt thereof.

Because of their ability to inhibit monoamine re-uptake, compounds of the invention may also be useful for treating diseases or conditions wherein insufficient synaptic levels of monoamine are implicated, such as for example: depression, obesity, sexual dysfunction, alcoholism, cocaine/opiate dependence, bulimia, anorexia nervosa, attention deficit hyperactivity disorder, obsessive-compulsive disorder, impulse control disorder, headache/migraine, and pain. Accordingly, the invention includes a therapeutic method for treating a disease or condition wherein insufficient synaptic levels of monoamine are implicated and inhibition of monoamine re-uptake is desired comprising administering to a mammal in need of such therapy, an effective amount of one or more compounds of formula I, or a pharmaceutically acceptable salt thereof.

The invention will now be illustrated by the following non-limiting examples in which unless otherwise stated:

a) synthetic intermediates were purchased from Aldrich Chemical Co. (Milwaukee, Wis.) and were used as received;

b) tetrahydrofuran (THF) was distilled from sodium hydride immediately prior to use;

c) all other reagents and solvents were purchased as reagent grade and used without further purification;

d) air-sensitive reactions were carried out under nitrogen;

e) yields were not optimized;

f) melting points were determined on a Haake-Buchler melting point apparatus and are uncorrected;

g) $^1$H NMR spectra were recorded on a 200 MHz IBM-Brucker spectrometer or a 300 MHZ GE spectrometer; NMR spectra are referenced to the deuterium lock frequency of the spectrometer, chemical shifts (in ppm) of residual solvents are observed at 7.26 ($CHCl_3$), 4.78 ($CD_3OD$);

h) preparative chromatography was performed on Harrison Research Chromatotron using Merck 60 PF254 silica gel or a preparative HPLC system (Rainin Instrument Co.) using a 41.1 mm id Dynamax silica gel column (delivering solvent at 80 mL/minute); Chromatographic resolution of racemates and determination of enantiomeric purity was performed by HPLC using a 250 mm×10 mm id Chiralcel column (mobile phase: I-PrOH-hexane-$Et_3$N or EtOH-hexane-$Et_3$N) at a flow rate of 2.4 mL/minute;

i) polarimetric measurements were performed with the aid of an Autopol III automatic polarimeter (Rudolph Research, Flanders, N.J., U.S.A.); and j) analytical TLC was carried out on Analtech GHLF silica gel glass plates, and visualization was aided by UV and/or methanolic iodine.

EXAMPLES

Example 1 cis-3-Phenylspiro[indan-1,3'-pyrrolidine]-2',5'-dione (1a)

A suspension of 10a (0.28 g, 11.0 mmol) in a mixture of 78% w/v $H_2SO_4$ (4 mL) and HOAc (10 mL) was heated at 125° C. for 1 hour. After cooling to room temperature, the reaction mixture was diluted with water (50 mL) and extracted with EtOAc (2×25 mL). The combined EtOAc extracts were washed with saturated aqueous $NaHCO_3$ (2×25 mL) and water (50 mL), dried ($Na_2SO_4$) and concentrated in vacuo to yield the desired imide as a buff solid (0.16 g, 53%). $^1$H NMR ($CDCl_3$) δ 2.57 (q, 1H, $CH_2$), 2.79 (q, 1H, $CH_2$), 2.90 (d, 1H, pyrrolidine $CH_2$), 3.08 (d, 1H, pyrrolidine $CH_2$), 4.45 (t, 1H, CH), 6.92–7.38 (m, 9H, Ar—H), 8.33 (bs, 1H, NH).

The intermediate 10a was prepared as follows.

a. 3-Phenylindan-1-one (6a). Polyphosphoric acid (10 g) was heated to 100° C. 3,3-Diphenylpropionic acid (1 g, ) was added and the suspension was stirred at 110° C. for 3.5 hours. Upon cooling to room temperature, the reaction was quenched with cold water (50 mL) accompanied by vigorous stirring. The resulting mixture was extracted with benzene (3×25 mL), and the organic extracts dried ($Na_2SO_4$) and concentrated under reduced pressure to yield a dark residue, which was dissolved in $CH_2Cl_2$ (5 mL) and passed through a short silica gel column (5% acetone-hexane) to afford the indanone as an amber syrup (0.7 g, 76%); $^1$H NMR ($CDCl_3$): δ 2.63 (dd, 1H, $CH_2$), 3.16 (dd, 1H, $CH_2$), 4.54 (q, 1H, CH), 7.10–7.83 (m, 9H, Ar—H).

b. 3-Phenylindan-1-ol (7a). Sodium borohydride (0.92 g, 23 mmol) was added portionwise to a solution of 3-phenylindan-1-one (1.2 g, 5.8 mmol) in methanol (50 mL). After completion of addition the reaction was stirred at room temperature for 2 hours. The solvent was removed in vacuo, and the residue was suspended in water (50 mL) and extracted with $CH_2Cl_2$ (3×25 mL). The combined extracts were dried ($Na_2SO_4$) and evaporated to afford the diastereomeric alcohol as a pale liquid (1.2 g, 95%); $^1$H NMR ($CDCl_3$): δ 1.88 (m, 2H, $CH_2$ and OH), 2.96 (m, 1H, $CH_2$), 4.15 (t, 1H, CH), 5.26 (t, 1H, CH), 6.94–7.5 (m, 9H, Ar—H).

c. 1-Chloro-3-phenylindane (8a). Anhydrous pyridine (0.3 mL, 3.6 mmol) was added to a solution of 3-phenylindan-1-ol (0.5 g, 2.4 mmol) in dry $CH_2Cl_2$ (10 mL). The resulting mixture was cooled in an ice bath and a solution of thionyl chloride (0.43 g, 3.6 mmol) in $CH_2Cl_2$ (15 mL) was added dropwise. The reaction mixture was stirred at room temperature for 1.5 hours, diluted with N HCl (25 mL) and extracted with $CH_2Cl_2$ (50 mL). The combined extracts were washed with 2N HCl (3×25 mL), dried ($Na_2SO_4$) and concentrated in vacuo to provide a diastereomeric mixture of the chloroindane as a dark liquid (0.45 g, 83%); $^1$H NMR ($CDCl_3$): δ 2.33 (m, 1H, $CH_2$), 2.82 and 3.17 (m, 1H, $CH_2$), 4.27 and 4.71 (t, 1H, CH), 5.39 (t, 1H, CH) and 5.57 (dd, 1H, CH), 6.96–7.56 (m, 9H, Ar—H).

d. 1-Cyano-3-phenylindane (9a). A mixture of 8a (2 g, 8.8 mmol), sodium cyanide (0.65 g, 13.1 mmol and a catalytic amount of KI was heated in anhydrous DMF (15 mL) at 70° C. for 20 hours. The reaction mixture was cooled to room temperature, diluted with water (50 mL) and extracted with ether (3×25 mL). The ether extracts were washed with water (5×50 mL), dried ($Na_2SO_4$) and concentrated under reduced pressure to a dark residue. Purification by radial flow chromatography (15% acetone-hexane) afforded the cyanoindane as a mixture of diastereomers (1 g, 53%); $^1$H NMR ($CDCl_3$): δ 2.29 (m, 1H, $CH_2$), 2.87 (m, 1H, $CH_2$), 4.20 and 4.62 (m, 2H, benzylic CH's), 6.96–7.50 (m, 9H, Ar—H). IR (neat) 2242 $cm^{-1}$ (CN).

e. 1-Cyano-1-cyanomethyl-3-phenylindane (10a). A solution of 9a (0.46 g, 2.1 mmol) in dry THF (30 mL) was added dropwise, over a 20 minute period, to a cooled solution (−78° C.) of lithium diisopropylamide (1.55 mL of a 2 M LDA solution in heptane/THF/ethylbenzene, 2.5 mmol) in dry THF (30 mL). The resulting mixture was stirred at −78° C. for 1 hour and warmed to −60° C. A solution of bromoacetonitrile (0.38 g, 3.2 mmol) in THF (10 mL) was added dropwise. The resulting mixture was gradually allowed to warm up to room temperature and stirred for 18 hours. The volatiles were evaporated in vacuo, the residue quenched with 3N HCl (50 mL) and extracted with $CH_2Cl_2$ (3×25 mL). The combined organic extracts were dried ($Na_2SO_4$) and concentrated under reduced pressure to a dark residue. Purification by radial flow using a mobile phase of 15% acetone-hexane provided the dinitrile as an amber syrup (0.28 g, 55%); $^1$H NMR ($CDCl_3$): δ 2.70 (m, 2H, indane $CH_2$), 2.94 (s, 2H, $CH_2$—CN), 4.47 (t, 1H, CH), 6.98–7.63 (m, 9H, Ar—H).

Example 2

3-(3,4-Dichlorophenyl)-6-methoxyspiro[indan-1,3'-pyrrolidin]-2',5'-dione (1c)

Using a procedure similar to that described in Example 1, except replacing the intermediate 10a used therein with the intermediate 10c, the title compound was prepared, yield, 52%; $^1$H NMR ($CDCl_3$): δ 2.57–2.8 (m, 2H, indane $CH_2$), 2.86 (d, 1H, pyrrolidine $CH_2$), 3.05 (d, 1H, pyrrolidine $CH_2$), 3.78 (s, 3H, $OCH_3$), 4.39 (t, 1H, CH), 6.60 (s, 1H, Ar—H), 6.80 (s, 2H, Ar—H), 7.15 (dd, 1H, Ar—H), 7.22 (s, 2H, Ar—H), 7.38 (m, 2H, Ar—H, imide NH).

The intermediate 10c was prepared as follows.

a. 6-Methoxy-3-(3',4'-dichlorophenyl)-1-indanone (6c). Using a procedure similar to that described in Example 1a, except replacing the 3,3-diphenylpropionic acid used therein with 3-(3',4'-dichlorophenyl)-3-(4-methoxyphenyl) propionic acid the indanone was prepared; $^1$H NMR (CDCl$_3$) δ 2.58 (dd, 1H, CH$_2$), 3.22 (dd, 1H, CH$_2$), 3.84 (s, 3H, OCH$_3$), 4.46 (t, 1H, CH), 6.92 (d, 1H, Ar—H̲), 7.12–7.25 (m, 4H, Ar—H̲), 7.29 (m, 1H, Ar—H̲).

b. 6-Methoxy-3-(3',4'-dichlorophenyl)-indan-1-ol (7c). Using a procedure similar to that described in Example 1b, except replacing the intermediate 6a used therein with the intermediate 6c, the indanol was prepared; $^1$H NMR (CDCl$_3$) δ 1.84–1.88 (m, 1H, CH$_2$), 2.04 (bd, 1H, OH), 2.99–3.03 (m, 1H, CH$_2$), 3.81 (s, 3H, OCH$_3$), 4.09 (t, 1H, CH), 5.25 (t, 1H, CH), 6.82–7.38 (m, 6H, Ar—H̲).

c. 1-Chloro-3-(3,4-dichlorophenyl)-6-methoxyindane (8c). Using a procedure similar to that described in Example 1c, except replacing the intermediate 7a used therein with the intermediate 7c, the chloride was prepared; $^1$H NMR (CDCl$_3$) δ 2.17–2.55 (m, 1H, CH$_2$), 2.80 and 3.22 (m, 1H, CH$_2$), 3.86 (s, 3H, OCH$_3$), 4.21 and 4.6 (t, 1H, CH), 5.33 and 5.45 (t, 1H, CH), 6.84–7.38 (m, 6H, Ar—H̲).

d. 1-Cyano-3-(3,4-dichlorophenyl)-6-methoxyindane (9c). Using a procedure similar to that described in Example 1d, except replacing the intermediate 8a used therein with the intermediate 8c, the cyano compound was prepared; $^1$H NMR (CDCl$_3$) δ 2.19–2.45 (m, 1H, CH$_2$), 2.80 and 3.15 (m, 1H, CH$_2$), 8.85 (s, 3H, OCH$_3$), 4.05–4.48 (m, 2H, CH), 6.80–7.40 (m, 6H, Ar—H̲). IR (neat): 2242 cm$^{-1}$ (CN).

e. 6-Methoxy-3-(3',4'-dichlorophenyl)-1-cyano-1-cyanomethylindane (10c). Using a procedure similar to that described in Example 1e, except replacing the intermediate 9a used therein with the intermediate 9c, the dicyano compound was prepared; $^1$H NMR (CDCl$_3$) δ 2.70 (m, 1H, indane CH$_2$), 2.94 (m, 3H, indane CH$_2$ and CH$_2$—CN), 3.86 (s, 3H, OCH$_3$), 4.44 (t, 1H, CH), 6.86–7.43 (m, 6H, Ar—H̲).

Example 3
3-Phenylspiro[indan-1,3'-pyrrolidine] (3a)

A solution of spiro[3-phenyl-1,3'-pyrroldine-2',5'-dione] 1a (0.97 g, 3.5 mmol) in dry THF (20 mL) was added dropwise to a suspension of lithium aluminum hydride (0.93 g, 24.5 mmol) in dry THF (30 mL) cooled in an ice bath. The reaction mixture was gradually warmed up to room temperature, refluxed for 20 hours, cooled to room temperature and slowly quenched by the sequential addition of water (1 mL), 15% aq.NaOH (3 mL) and water (3 mL). The resulting suspension was filtered through Celite, and the filtrate was concentrated in vacuo. The residue was redissolved CH$_2$Cl$_2$ (25 mL), and the solution dried (Na$_2$SO$_4$) and concentrated in vacuo to afford 0.89 g (87%) of the amine as a tan liquid. The hydrochloride was prepared from methanolic HCl and recrystallized from i-PrOH-ether. $^1$H NMR (free base) (CDCl$_3$) δ 1.83 (m, 4H, CH$_2$), 2.98–3.35 (m, 5H, CH$_2$ and NH̲), 4.39 (t, 1H, CH), 6.92–7.34 (m, 9H, Ar—H̲). Elemental analysis calcd for C$_{18}$H$_{19}$N.HCl: C, 75.76; H, 7.07; N, 4.91. Found: C, 75.95; H, 7.28; N, 4.35.

Example 4
3-(3,4-Dichlorophenyl)-6-methoxyspiro[indan-1,3'-pyrrolidine] (3c)

Using a procedure similar to that described in Example 3, except replacing the 1a used therein with the 1c, the title compound was prepared; $^1$H NMR (free base) (CDCl$_3$): δ 1.40–2.05 (m, 4H, CH$_2$), 2.45 (m, 2H, CH$_2$), 2.98–3.65 (m, 3H, CH$_2$and NH̲), 3.80 (s, 3H, OCH$_3$),4.28 (t, 1H, CH), 6.71–6.81 (m, 3H, Ar—H̲), 7.0 (d, 1H, Ar—H̲), 7.21–7.38 (m, 2H, Ar—H̲). Elemental analysis calcd. for C$_{19}$H$_{19}$Cl$_2$NO.HCl: C, 59.52; H, 5.26; N, 3.66. Found: C, 59.61; H, 5.57; 2.95.

Example 5
3-(3,4-Dichlorophenyl)-6-hydroxyspiro[indan-1,3'-pyrrolidine] (3d)

Spiro[3-(3",4"-dichlorophenyl)-6-methoxyindan-1,3'-pyrrolidine] from Example 4 (0.24 g) was refluxed in a mixture of HOAc and 48% aqueous HBr (5 mL each) for 6 hours. Excess acid was quenched with saturated aqueous NaHCO$_3$ and extracted with EtOAc (2×25 mL). The organics were dried (Na$_2$SO$_4$) and solvent stripped off in vacuo to afford the title compound as a tan liquid ( 0.16 g, 69.5%). The HCl salt was made in methanolic HCl and recrystallized from i-PrOH-ether as a dark solid. $^1$H NMR (free base) (CDCl$_3$): δ 1.82–2.05 (m, 3H, CH$_2$), 2.46 (m, 1H, CH$_2$), 3.05–3.43 (m, 5H, CH$_2$ and NH̲), 4.24 (t, 1H, CH), 5.60 (bs, 1H, OH̲), 6.65–6.81 (m, 2H, ArH̲), 7.0 (d, 1H, Ar—H̲), 7.23–7.40 (m, 2H, Ar—H̲).

Example 6
1'-Cyclopropylmethyl-3-phenylspiro[indan-1,3'-pyrrolidine] hydrochloride (4a)

A mixture of spiro[3-phenylindan-1,3'-pyrrolidine] (0.65 g, 2.61 mmol) from Example 3, cyclopropylmethyl bromide (0.43 g, 3.10 mmol) and anhydrous K$_2$CO$_3$ (0.43 g, 3.10 mmol) was stirred in DMF (10 mL) at room temperature for 20 hours. The mixture was diluted with CH$_2$Cl$_2$ (25 mL) and filtered to remove insoluble material. Concentration of the filtrate provided the crude product as a dark residue. The title compound was isolated by radial flow chromatography using (15% acetone-hexane+trace Et$_3$N) (0.27 g, 35%). The hydrochloride salt was prepared from methanolic HCl and recrystallized from i-PrOH-ether. $^1$H NMR (CDCl$_3$) δ 0.12 (m, 2H, CH$_2$), 0.47 (m, 2H, CH$_2$), 0.94 (m, 1H, CH), 1.68–3.21 (m, 10H, indane and pyrrolidine CH$_2$ and N—CH$_2$), 4.31 (t, 1H, CH), 6.86–7.44 (m, 9H, Ar—H̲). Elemental analysis calcd. for C$_{22}$H$_{25}$N HCl: C, 77.84; H, 7.73; N, 4.13. Found: C, 77.71; H, 7.80; N, 4.13.

Example 7
cis-3-Phenylspiro[indan-1,3'-pyrrolidine]-2',5'-dione (1a) and trans-3-Phenylspiro[indan-1,3'-pyrrolidine]-2',5'-dione (2a)

A suspension of a regioisomeric mixture of 10a and 12a (10.3 g, 0.40 mol) in glacial HOAc (50 mL) and 78% v/v H$_2$SO$_4$ (35 mL) was heated at 125° C. for 1 hour, and allowed to cool to room temperature. The solvent was removed in vacuo to provide a residue which was treated with treated with water (100 mL), and extracted with EtOAc (3×50 mL). The combined organic extracts were washed with 5% aq.NaHCO$_3$ (3×25 mL), dried (Na$_2$SO$_4$) and concentrated in vacuo. The residue was passed through a short silica gel column using a mobile phase of 25% acetone-hexane. Concentration of the eluent provided the diastereomeric imide as a sand colored solid (3.4 g, 31%); $^1$H NMR (CDCl$_3$) δ 2.2–3.3 (m, 4H, indanyl CH$_2$ and CH̲$_2$—CN), 4.5–4.7 and 4.8 (three t, 1H, indanyl CH), 6.9–7.4 (m, 9H, Ar—H), 8.0 and 8.2 (two bs, 1H, imide NH̲); EIMS m/z 277.11 (M$^+$).

The intermediate mixture of 10a and 12a was prepared as follows.

a. Ethyl 3-Phenyl-1-indanylidenecyanoacetate (11a). A mixture of 3-phenyl-1-indanone (3 g, 14.4 mmol), pyrrolidine (0.25 g, 3.6 mmol), acetic acid (9.6 mmol) and ethyl cyanoacetate (1.62 g, 14.4 mol) in benzene (50 mL) was refluxed with azeotropic removal of water for 17 hours. The reaction mixture was cooled to room temperature, diluted with benzene (50 mL) and washed consecutively with 5% aq.NaHCO$_3$ (2×25 mL) and water (50 mL). The organic extract was dried (Na$_2$SO$_4$) and concentrated in vacuo to afford the Claisen-Schmidt adduct as a sand colored solid (4.0 g, 92%); $^1$H NMR (CDCl$_3$) δ 1.40 ( t, 3H, CH$_3$), 3.40–3.50 (m, 1H, indanyl CH$_2$), 4.05–4.15 (dd, 1H, indanyl CH$_2$), 4.30 (q, 2H, CH$_2$), 4.50 (q, 1H, indanyl CH), 7.05–7.55 (m, 9H, Ar—H).

b. 3-Phenyl-1-cyano-1-cyanomethylindane (10a and 12a). A mixture of 11a (1 g, 3.29 mmol) and KCN (0.53 g, 8.24 mmol) in ethanol (10 mL) and water (1.7 mL) was heated under nitrogen atmosphere at 65° C. for 18 hours. The reaction mixture was cooled to room temperature and the solvent was removed under reduced. The resulting solid residue was treated with water and extracted with CH$_2$Cl$_2$ (2×25 mL). The combined organic extracts were dried (Na$_2$SO$_4$) and concentrated under reduced pressure to provide the crude product. Purification by radial flow chromatography using a mobile phase of 20% acetone-hexane afforded the dinitrile as a mixture of diastereomers 10a and 12a (0.41 g, 48%). This mixture was not readily amenable to chromatographic separation. $^1$H NMR (CDCl$_3$) δ 2.35–2.45 (q, 1H, indanyl CH$_2$), 2.75–3.30 (m, 3H, indanyl CH$_2$ and CH$_2$—CN), 4.50–4.70 (two t, 1H, indanyl CH), 7.0–7.6 (m, 9H, Ar—H). Elemental analysis calcd. for C$_{18}$H$_{14}$N$_2$: C, 83.68; H, 5.47; N, 10.85; Found: C, 82.32; H, 5.45; N, 9.87.

Example 8 cis-3-(3,4-Dichlorophenyl)spiro[indan-1,3'-pyrrolidine]-2',5'-dione (1b) and trans-3-(3,4-Dichlorophenyl)spiro[indan-1,3'-pyrrolidine]-2',5'-dione (2b)

Using a procedure similar to that described in Example 7, except replacing the mixture of 10a and 12a used therein with a mixture of 10b and 12b, the title compounds were prepared; $^1$H NMR (CDCl$_3$) δ 1.9–3.8 (m, 4H, indanyl and pyrrolidinyl CH$_2$), 4.4–4.8 (m, 1H, indanyl CH), 6.9–7.5 (m, 7H, Ar—H). EIMS m/z 345 (M$^+$), 346 (M+H)$^+$.

The intermediate mixture of 10b and 12b was prepared as follows.

a. Ethyl 3-(3,4-dichlorophenyl)-1-indanylidenecyanoacetate (11b). Using a procedure similar to that described in Example 7a, except replacing the 3-phenyl-1-indanone used therein, with 3-(3,4-dichlorophenyl)-1-indanone, the indanylidine compound was prepared; $^1$H NMR (CDCl$_3$) δ 1.4 (m, 3H, CH$_3$), 3.3–3.5 (m, 1H, indanyl CH$_2$), 4.1 (dd, 1H, indanyl CH$_2$), 4.3 (m, 2H, CH$_2$), 4.4 (q, 1H, indanyl CH), 6.9–7.6 (m, 7H, Ar—H).

b. cis and trans-3-(3,4-Dichlorophenyl)-1-cyano-1-cyanomethylindane (10b and 12b). Using a procedure similar to that described in Example 7b, except replacing the 11a used therein with 11b, the dicyano compound was prepared. Purification by HPLC (10% isopropyl alcohol-hexane) yielded 10b and 12b; $^1$H NMR (CDCl$_3$) δ 2.0–2.4 (m, 3H), 2.7–3.2 (m, 1H), 4.6 (m, 1H, CH), 7.0–7.6 (m, 7H, Ar—H).

The intermediate 3-(3,4-dichlorophenyl)-1-indanone was prepared using a procedure similar to that described in Example 1a except replacing the 3,3-diphenylpropionic acid used therein with 3-(3,4-dichlorophenyl)-3-phenylpropionic acid.

Example 9 cis-3-Phenylspiro[indan-1,3'-pyrrolidine] (3a) and trans-3-Phenylspiro[indan-1,3'-pyrrolidine] (5a)

A solution of the diastereomeric mixture of 1a and 2a from Example 7 (3.4 g, 12.2 mmol) in anhydrous THF (50 mL) was added dropwise under nitrogen to a suspension of LiAlH$_4$ (2.8 g, 73.0 mmol) in anhydrous THF (100 mL). Following the addition, the reaction mixture was refluxed for 16 hours, cooled to room temperature and carefully quenched by the dropwise addition of water (3.4 mL), 10% aq.NaOH (10.2 mL) and water (10.2 mL). The resulting suspension was filtered, the precipitate washed with EtOAc (150 mL) and discarded. The filtrate was dried (Na$_2$SO$_4$) and concentrated under reduced pressure. Purification by HPLC on silica gel (5% MeOH—CH$_2$Cl$_2$ plus trace Et$_3$N) afforded the title spiroindanamines 3a and 5a; $^1$H NMR (CDCl$_3$) δ 1.9–4.0 (m, 9H, indanyl and pyrrolidinyl CH$_2$ and NH), 4.4 (m, 1H, indanyl CH), 6.9–7.4 (m, 9H, Ar—H).

Example 10 cis-3-(3,4-Dichlorophenyl)spiro[indan-1,3'-pyrrolidine] (3b) and trans-3-(3,4-Dichlorophenyl)spiro[indan-1,3'-pyrrolidine] (5b)

A solution of the diastereomeric mixture 1b/2b (2.7 g) from Example 8 in anhydrous THF (30 mL) was added dropwise under nitrogen to 1M borane THF (100 mL). The reaction was then allowed to reflux for 18 hours after which it was cooled to room temperature and concentrated in vacuo. The residue was carefully quenched with 6N HCl (75 mL) and the resulting solution was refluxed for 18 hours. After cooling to room temperature, the reaction mixture was washed with CH$_2$Cl$_2$ and the organic layer discarded. The acidic layer was concentrated in vacuo, and the residue was made basic with 10% aq.NaOH and extracted with EtOAc (3×50 mL). The combined organic extracts were dried (Na$_2$SO$_4$) and concentrated under reduced pressure. Purification by HPLC on a silica gel column (5% MeOH—CH$_2$Cl$_2$) gave the spiroindanamines 3b and 5b; $^1$H NMR (CDCl$_3$) δ 1.9–3.7 (m, 8H, indanyl and pyrrolidinyl CH$_2$), 4.3 (m, 1H, indanyl CH), 4.8 (bs, 1H, NH), 6.8–7.4 (m, 7H, Ar—H).

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

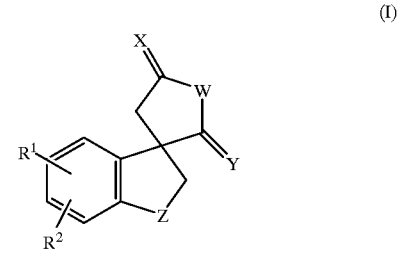

wherein

X and Y are each independently two hydrogens or thioxo;

R$^1$ and R$^2$ are each independently hydrogen, halo, hydroxy, cyano, N(R$_a$)(R$_b$), (C$_1$–C$_6$)alkyl, (C$_1$–C$_6$)alkoxy, (C$_1$–C$_6$)alkanoyl, (C$_1$C$_6$)alkanoyloxy, or (C$_3$–C$_6$)cycloalkyl; wherein R$_a$ and R$_b$ are each independently hydrogen, (C$_1$–C$_6$)alkyl, (C$_1$–C$_6$)alkanoyl, phenyl, benzyl, or phenethyl;

W is —N(R$_c$)—;

Z is —N(R$_d$)— or —C(R$^e$)(R$_f$)—;

R$_c$, R$_d$, R$_e$, and R$_f$ are each independently hydrogen, (C$_1$–C$_6$)alkyl, (C$_3$–C$_6$)cycloalkyl, aryl, heteroaryl, aryl (C$_1$–C$_6$)alkyl, heteroaryl(C$_1$–C$_6$)alkyl, (C$_1$–C$_6$) alkanoyl, arylcarbonyl, heteroarylcarbonyl, arylcarbonyl($C_1$–$C_6$)alkyl, or heteroarylcarbonyl ($C_1$–$C_6$)alkyl, wherein any aryl or heteroaryl may optionally be substituted on carbon by 1, 2 or 3 U;

each U is independently halo, nitro, cyano, hydroxy, trifluoromethyl, trifluoromethoxy, ($C_1$–$C_6$)alkyl, ($C_3$–$C_6$)cycloalkyl, ($C_1$–$C_6$)alkoxy, ($C_1$–$C_6$)alkanoyl, ($C_2$–$C_6$)alkanoyloxy, C(=O)O$R_g$, C(=O)N$R_h R_i$, or N$R_j R_k$;

wherein any ($C_1$–$C_6$)alkyl, ($C_3$–$C_6$)cycloalkyl, or ($C_1$–$C_6$) alkoxy in $R^1$, $R^2$, $R_c$, $R_d$, $R_e$, $R_f$, or U may optionally be substituted on carbon by 1, 2 or 3 V;

each V is independently halo, nitro, cyano, hydroxy, ($C_3$–$C_6$)cycloalkyl, ($C_1$–$C_6$)alkoxy, ($C_1$–$C_6$)alkanoyl, ($C_2$–$C_6$)alkanoyloxy, C(=O)O$R_m$, C(=O)N$R_n R_o$, N$R_p R_q$;

each $R_g$, $R_h$, $R_i$, $R_m$, $R_n$, and $R_o$ is independently hydrogen or ($C_1$–$C_6$)alkyl; and each $R_j$, $R_k$, $R_p$, and $R_q$ is independently hydrogen, ($C_1$–$C_6$)alkyl, ($C_1$–$C_6$)alkanoyl, phenyl, benzyl, or phenethyl; or a pharmaceutically acceptable salt thereof.

2. The compound of claim 1 wherein X and Y are each two hydrogens.

3. The compound of claim 1 wherein Z is —N($R_d$)—.

4. The compound of claim 1 wherein Z is —C($R_e$)($R_f$)—.

5. The compound of claim 1 which is 3-phenylspiro[indan-1,3'-pyrrolidine].

6. The compound of claim 1 which is 3-(3,4-dichlorophenyl)-6-methoxyspiro[indan-1,3'-pyrrolidine].

7. A compound of formula I:

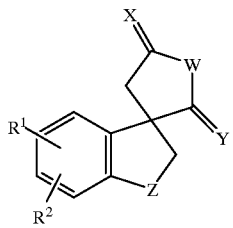

(I)

wherein

X and Y are each independently two hydrogens, oxo, or thioxo;

$R^1$ and $R^2$ are each independently hydrogen, halo, hydroxy, cyano, N($R_a$)($R_b$), ($C_1$–$C_6$)alkyl, ($C_1$–$C_6$) alkoxy, ($C_1$–$C_6$)alkanoyl, ($C_1$–$C_6$)alkanoyloxy, or ($C_3$–$C_6$)cycloalkyl; wherein $R_a$ and $R_b$ are each independently hydrogen, ($C_1$–$C_6$)alkyl, ($C_1$–$C_6$)alkanoyl, phenyl, benzyl, or phenethyl;

W is —N($R_c$)—;

Z is —N($R_d$)— or —C($R_e$)($R_f$)—;

$R_c$ is ($C_3$–$C_6$)cycloalkyl, aryl, heteroaryl, aryl($C_1$–$C_6$) alkyl, heteroaryl($C_1$–$C_6$)alkyl, ($C_1$–$C_6$)alkanoyl, arylcarbonyl, heteroarylcarbonyl, arylcarbonyl($C_1$–$C_6$) alkyl, or heteroarylcarbonyl($C_1$–$C_6$)alkyl, wherein any aryl or heteroaryl may optionally be substituted on carbon by 1, 2 or 3 U;

$R_d$, $R_e$, and $R_f$ are each independently hydrogen, ($C_1$–$C_6$) alkyl, ($C_3$–$C_6$)cycloalkyl, aryl, heteroaryl, aryl($C_1$–$C_6$) alkyl, heteroaryl($C_1$–$C_6$)alkyl, ($C_1$–$C_6$)alkanoyl, arylcarbonyl, heteroarylcarbonyl, arylcarbonyl($C_1$–$C_6$) alkyl, or heteroarylcarbonyl($C_1$–$C_6$)alkyl, wherein any aryl or heteroaryl may optionally be substituted on carbon by 1, 2 or 3 U;

each U is independently halo, nitro, cyano, hydroxy, trifluoromethyl, trifluoromethoxy, ($C_1$–$C_6$)alkyl, ($C_3$–$C_6$)cycloalkyl, ($C_1$–$C_6$)alkoxy, ($C_1$–$C_6$)alkanoyl, ($C_2$–$C_6$)alkanoyloxy, C(=O)O$R_g$, C(=O)N$R_h R_i$, or N$R_j R_k$;

wherein any ($C_1$–$C_6$)alkyl, ($C_3$–$C_6$)cycloalkyl, or ($C_1$–$C_6$) alkoxy in $R^1$, $R^2$, $R_c$, $R_d$, $R_e$, $R_f$, or U may optionally be substituted on carbon by 1, 2 or 3 V;

each V is independently halo, nitro, cyano, hydroxy, ($C_3$–$C_6$)cycloalkyl, ($C_1$–$C_6$)alkoxy, ($C_1$–$C_6$)alkanoyl, ($C_2$–$C_6$)alkanoyloxy, C(=O)O$R_m$, C(=O)N$R_n R_o$, or N$R_p R_q$;

each $R_g$, $R_h$, $R_i$, $R_m$, $R_n$, and $R_o$ is independently hydrogen or ($C_1$–$C_6$)alkyl; and each $R_j$, $R_k$, $R_p$, and $R_q$ is independently hydrogen, ($C_1$–$C_6$)alkyl, ($C_1$–$C_6$)alkanoyl, phenyl, benzyl, or phenethyl;

or a pharmaceutically acceptable salt thereof.

8. A compound of formula I:

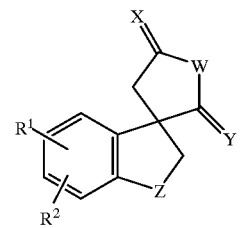

(I)

wherein

X and Y are each independently two hydrogens, oxo, or thioxo;

$R^1$ and $R^2$ are each independently hydrogen, halo, hydroxy, cyano, N($R_a$)($R_b$), ($C_1$–$C_6$)alkyl, ($C_1$–$C_6$) alkoxy, ($C_1$–$C_6$)alkanoyl, ($C_1$–$C_6$)alkanoyloxy, or ($C_3$–$C_6$)cycloalkyl; wherein $R_a$ and $R_b$ are each independently hydrogen, ($C_1$–$C_6$)alkyl, ($C_1$–$C_6$)alkanoyl, phenyl, benzyl, or phenethyl;

W is —N($R_c$)—;

Z is —N($R_d$)—;

$R_c$ and $R_d$ are each independently hydrogen, ($C_1$–$C_6$) alkyl, ($C_3$–$C_6$)cycloalkyl, aryl, heteroaryl, aryl($C_1$–$C_6$) alkyl, heteroaryl($C_1$–$C_6$)alkyl, ($C_1$–$C_6$)alkanoyl, arylcarbonyl, heteroarylcarbonyl, arylcarbonyl($C_1$–$C_6$) alkyl, or heteroarylcarbonyl($C_1$–$C_6$)alkyl, wherein any aryl or heteroaryl may optionally be substituted on carbon by 1, 2 or 3 U;

each U is independently halo, nitro, cyano, hydroxy, trifluoromethyl, trifluoromethoxy, ($C_1$–$C_6$)alkyl, ($C_3$–$C_6$)cycloalkyl, ($C_1$–$C_6$)alkoxy, ($C_1 C_6$)alkanoyl, ($C_2$–$C_6$)alkanoyloxy, C(=O)O$R_g$, C(=O)N$R_h R_i$, or N$R_j R_k$;

wherein any ($C_1$–$C_6$)alkyl, ($C_3$–$C_6$)cycloalkyl, or ($C_1$–$C_6$) alkoxy in $R^1$, $R^2$, $R_c$, $R_d$, or U may optionally be substituted on carbon by 1, 2 or 3 V;

each V is independently halo, nitro, cyano, hydroxy, ($C_3$–$C_6$)cycloalkyl, ($C_1$–$C_6$)alkoxy, ($C_1$–$C_6$)alkanoyl, ($C_2$–$C_6$)alkanoyloxy, C(=O)O$R_m$, C(=O)N$R_n R_o$, or N$R_p R_q$;

each $R_g$, $R_h$, $R_i$, $R_m$, $R_n$, and $R_o$ is independently hydrogen or ($C_1$–$C_6$)alkyl; and each $R_j$, $R_k$, $R_p$, and $R_q$ is independently hydrogen, $(C_1-C_6)$alkyl, $(C_1-C_6)$alkanoyl, phenyl, benzyl, or phenethyl;

or a pharmaceutically acceptable salt thereof.

9. A compound of formula I:

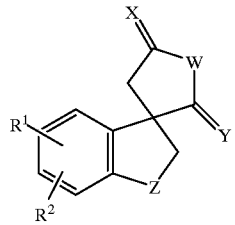

(I)

wherein

X and Y are each independently two hydrogens, oxo, or thioxo;

$R^1$ and $R^2$ are each independently hydrogen, halo, hydroxy, cyano, $N(R_a)(R_b)$, $(C_1-C_6)$alkyl, $(C_1-C_6)$alkoxy, $(C_1-C_6)$alkanoyl, $(C_1-C_6)$alkanoyloxy, or $(C_3-C_6)$cycloalkyl; wherein $R_a$ and $R_b$ are each independently hydrogen, $(C_1-C_6)$alkyl, $(C_1-C_6)$alkanoyl, phenyl, benzyl, or phenethyl;

W is —$N(R_c)$—;

Z is —$N(R_d)$— or —$C(R_e)(R_f)$—;

$R_c$ is cyclopropylmethyl;

$R_d$, $R_e$, and $R_f$ are each independently hydrogen, $(C_1-C_6)$alkyl, $(C_3-C_6)$cycloalkyl, aryl, heteroaryl, aryl$(C_1-C_6)$alkyl, heteroaryl$(C_1-C_6)$alkyl, $(C_1-C_6)$alkanoyl, arylcarbonyl, heteroarylcarbonyl, arylcarbonyl$(C_1-C_6)$alkyl, or heteroarylcarbonyl$(C_1-C_6)$alkyl, wherein any aryl or heteroaryl may optionally be substituted on carbon by 1, 2 or 3 U;

each U is independently halo, nitro, cyano, hydroxy, trifluoromethyl, trifluoromethoxy, $(C_1-C_6)$alkyl, $(C_3-C_6)$cycloalkyl, $(C_1-C_6)$alkoxy, $(C_1-C_6)$alkanoyl, $(C_2-C_6)$alkanoyloxy, $C(=O)OR_g$, $C(=O)NR_hR_i$, or $NR_jR_k$;

wherein any $(C_1-C_6)$alkyl, $(C_3-C_6)$cycloalkyl, or $(C_1-C_6)$alkoxy in $R^1$, $R^2$, $R_d$, $R_e$, $R_f$, or U may optionally be substituted on carbon by 1, 2 or 3 V;

each V is independently halo, nitro, cyano, hydroxy, $(C_3-C_6)$cycloalkyl, $(C_1-C_6)$alkoxy, $(C_1-C_6)$alkanoyl, $(C_2-C_6)$alkanoyloxy, $C(=O)OR_m$, $C(=O)NR_nR_o$, $NR_pR_q$;

each $R_g$, $R_h$, $R_i$, $R_m$, $R_n$ and $R_o$ is independently hydrogen or $(C_1-C_6)$alkyl; and each $R_j$, $R_k$, $R_p$, and $R_q$ is independently hydrogen, $(C_1-C_6)$alkyl, $(C_1-C_6)$alkanoyl, phenyl, benzyl, or phenethyl;

or a pharmaceutically acceptable salt thereof.

10. A compound of formula I:

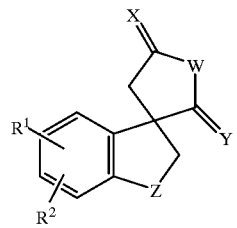

(I)

wherein

X and Y are each independently two hydrogens, oxo, or thioxo;

$R^1$ and $R^2$ are each independently hydrogen, halo, hydroxy, cyano, $N(R_a)(R_b)$, $(C_1-C_6)$alkyl, $(C_1-C_6)$alkoxy, $(C_1-C_6)$alkanoyl, $(C_1-C_6)$alkanoyloxy, or $(C_3-C_6)$cycloalkyl; wherein $R_a$ and $R_b$ are each independently hydrogen, $(C_1-C_6)$alkyl, $(C_1-C_6)$alkanoyl, phenyl, benzyl, or phenethyl;

W is —$N(R_c)$—;

Z is —$C(R_e)(R_f)$—;

$R_c$ is hydrogen, $(C_1-C_6)$alkyl, $(C_3-C_6)$cycloalkyl, aryl, heteroaryl, aryl$(C_1-C_6)$alkyl, heteroaryl$(C_1-C_6)$alkyl, $(C_1-C_6)$alkanoyl, arylcarbonyl, heteroarylcarbonyl, arylcarbonyl$(C_1-C_6)$alkyl, or heteroarylcarbonyl $(C_1-C_6)$alkyl, wherein any aryl or heteroaryl may optionally be substituted on carbon by 1, 2 or 3 U;

$R_e$ is hydrogen and $R_f$ is phenyl or 3,4-dichlorophenyl;

each U is independently halo, nitro, cyano, hydroxy, trifluoromethyl, trifluoromethoxy, $(C_1-C_6)$alkyl $(C_3-C_6)$cycloalkyl, $(C_1-C_6)$alkoxy, $(C_1-C_6)$alkanoyl, $(C_2-C_6)$alkanoyloxy, $C(=O)OR_g$, $C(=O)NR_hR_i$, or $NR_jR_k$;

wherein any $(C_1-C_6)$alkyl, $(C_3-C_6)$cycloalkyl, or $(C_1-C_6)$alkoxy in $R^1$, $R^2$, $R_c$, $R_e$, $R_f$, or U may optionally be substituted on carbon by 1, 2 or 3 V;

each V is independently halo, nitro, cyano, hydroxy, $(C_3-C_6)$cycloalkyl, $(C_1-C_6)$alkoxy, $(C_1-C_6)$alkanoyl, $(C_2-C_6)$alkanoyloxy, $C(=O)OR_m$, $C(=O)NR_nR_o$, $NR_pR_q$;

each $R_g$, $R_h$, $R_i$, $R_m$, $R_n$, and $R_o$ is independently hydrogen or $(C_1-C_6)$alkyl; and each $R_j$, $R_k$, $R_p$, and $R_q$ is independently hydrogen, $(C_1-C_6)$alkyl, $(C_1-C_6)$alkanoyl, phenyl, benzyl, or phenethyl;

or a pharmaceutically acceptable salt thereof.

11. A compound of formula I:

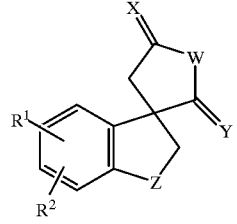

(I)

wherein

X and Y are each independently two hydrogens or oxo;

R$^1$ and R$^2$ are each independently hydrogen, hydroxy, or (C$_1$–C$_6$)alkoxy;

W is —N(R$_c$)—;

R$_c$ is hydrogen, (C$_3$–C$_6$)cycloalkyl, or (C$_1$–C$_6$)alkyl optionally substituted with (C$_3$–C$_6$)cycloalkyl;

Z is —C(R$_e$)(R$_f$)—;

R$_e$ is hydrogen; R$_f$ is aryl, optionally substituted on carbon by 1, 2 or 3 U;

each U is independently halo, hydroxy, trifluoromethoxy, (C$_1$–C$_6$)alkyl, (C$_3$–C$_6$)cycloalkyl, (C$_1$–C$_6$)alkoxy, or NR$_j$R$_k$; and R$_j$ and R$_k$ are each independently hydrogen or (C$_1$–C$_6$) alkyl; or a pharmaceutically acceptable salt thereof.

12. A compound of formula I:

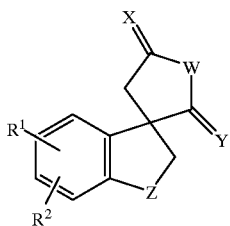

(I)

wherein

X and Y are each independently two hydrogens, oxo, or thioxo;

R$^1$ and R$^2$ are each independently halo, hydroxy, cyano, N(R$_a$)(R$_b$), (C$_1$–C$_6$)alkoxy, (C$_1$–C$_6$)alkanoyl, (C$_1$–C$_6$)alkanoyloxy, or (C$_3$–C$_6$)cycloalkyl; wherein R$_a$ and R$_b$ are each independently hydrogen, (C$_1$–C$_6$)alkyl, (C$_1$–C$_6$)alkanoyl, phenyl, benzyl, or phenethyl;

W is —N(R$_c$)—;

Z is —N(R$_d$)— or —C(R$_e$)(R$_f$)—;

R$_c$, R$_d$, R$_e$, and R$_f$ are each independently hydrogen, (C$_1$–C$_6$)alkyl, (C$_3$–C$_6$)cycloalkyl, aryl, heteroaryl, aryl (C$_1$–C$_6$)alkyl, heteroaryl(C$_1$–C$_6$)alkyl, (C$_1$–C$_6$) alkanoyl, arylcarbonyl, heteroarylcarbonyl, arylcarbonyl(C$_1$–C$_6$)alkyl, or heteroarylcarbonyl (C$_1$–C$_6$)alkyl, wherein any aryl or heteroaryl may optionally be substituted on carbon by 1, 2 or 3 U;

each U is independently halo, nitro, cyano, hydroxy, trifluoromethyl, trifluoromethoxy, (C$_1$–C$_6$)alkyl, (C$_3$–C$_6$)cycloalkyl, (C$_1$–C$_6$)alkoxy, (C$_1$–C$_6$)alkanoyl, (C$_2$–C$_6$)alkanoyloxy, C(=O)OR$_g$, C(=O)NR$_h$R$_i$, or NR$_j$R$_k$;

wherein any (C$_1$–C$_6$)alkyl, (C$_3$–C$_6$)cycloalkyl, or (C$_1$–C$_6$) alkoxy in R$^1$, R$^2$, R$_c$, R$_d$, R$_e$, R$_f$, or U may optionally be substituted on carbon by 1, 2 or 3 V;

each V is independently halo, nitro, cyano, hydroxy, (C$_3$–C$_6$)cycloalkyl, (C$_1$–C$_6$)alkoxy, (C$_1$–C$_6$)alkanoyl, (C$_2$–C$_6$)alkanoyloxy, C(=O)OR$_m$, C(=O)NR$_n$R$_o$, NR$_p$R$_q$;

each R$_g$, R$_h$, R$_i$, R$_m$, R$_n$, and R$_o$ is independently hydrogen or (C$_1$–C$_6$)alkyl; and each R$_j$, R$_k$, R$_p$, and R$_q$ is independently hydrogen, (C$_1$–C$_6$)alkyl, (C$_1$–C$_6$)alkanoyl, phenyl, benzyl, or phenethyl;

or a pharmaceutically acceptable salt thereof.

13. A pharmaceutical composition comprising a compound of any one of claims 1 or 7 to 12 and a pharmaceutically acceptable carrier.

14. A therapeutic method comprising inhibiting monoamine re-uptake in a mammal by administering to a in a mammal in need of such therapy, an effective amount of a compound of formula I:

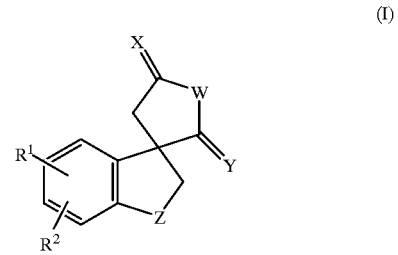

(I)

wherein

X and Y are each independently two hydrogens, oxo, or thioxo;

R$^1$ and R$^2$ are each independently hydrogen, halo, hydroxy, cyano, N(R$_a$)(R$_b$), (C$_1$–C$_6$)alkyl, (C$_1$–C$_6$) alkoxy, (C$_1$–C$_6$)alkanoyl, (C$_1$–C$_6$)alkanoyloxy, or (C$_3$–C$_6$)cycloalkyl; wherein R$_a$ and R$_b$ are each independently hydrogen, (C$_1$–C$_6$)alkyl, (C$_1$–C$_6$)alkanoyl, phenyl, benzyl, or phenethyl;

W is —N(R$_c$)—;

Z is —N(R$_d$)— or —C(R$_e$)(R$_f$)—;

R$_c$, R$_d$, R$_e$, and R$_f$ are each independently hydrogen, (C$_1$–C$_6$)alkyl, (C$_3$–C$_6$)cycloalkyl, aryl, heteroaryl, aryl (C$_1$–C$_6$)alkyl, heteroaryl(C$_1$–C$_6$)alkyl, (C$_1$–C$_6$) alkanoyl, arylcarbonyl, heteroarylcarbonyl, arylcarbonyl(C$_1$–C$_6$)alkyl, or heteroarylcarbonyl (C$_1$–C$_6$)alkyl, wherein any aryl or heteroaryl may optionally be substituted on carbon by 1, 2 or 3 U;

each U is independently halo, nitro, cyano, hydroxy, trifluoromethyl, trifluoromethoxy, (C$_1$–C$_6$)alkyl, (C$_3$–C$_6$)cycloalkyl, (C$_1$–C$_6$)alkoxy, (C$_1$–C$_6$)alkanoyl, (C$_2$–C$_6$)alkanoyloxy, C(=O)OR$_g$, C(=O)NR$_h$R$_i$, or NR$_j$R$_k$;

wherein any (C$_1$–C$_6$)alkyl, (C$_3$–C$_6$)cycloalkyl, or (C$_1$–C$_6$) alkoxy in R$^1$, R$^2$, R$_c$, R$_d$, R$_e$, R$_f$, or U may optionally be substituted on carbon by 1, 2 or 3 V;

each V is independently halo, nitro, cyano, hydroxy, (C$_3$–C$_6$)cycloalkyl, (C$_1$–C$_6$)alkoxy, (C$_1$–C$_6$)alkanoyl, (C$_2$–C$_6$)alkanoyloxy, C(=O)OR$_m$, C(=O)NR$_n$R$_o$, NR$_p$R$_q$;

each R$_g$, R$_h$, R$_i$, R$_m$, R$_n$, and R$_o$ is independently hydrogen or (C$_1$–C$_6$)alkyl; and each R$_j$, R$_k$, R$_p$, and R$_q$ is independently hydrogen, (C$_1$–C$_6$)alkyl, (C$_1$–C$_6$)alkanoyl, phenyl, benzyl, or phenethyl; or or a pharmaceutically acceptable salt thereof.

15. A therapeutic method comprising treating a disease or condition wherein inhibition of monoamine re-uptake is desired, by administering to a mammal in need of such therapy, an effective amount of one or more compounds of formula I:

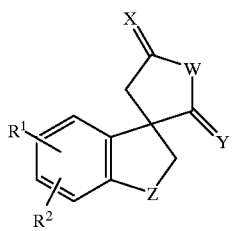

(I)

wherein
- X and Y are each independently two hydrogens, oxo, or thioxo;
- $R^1$ and $R^2$ are each independently hydrogen, halo, hydroxy, cyano, $N(R_a)(R_b)$, $(C_1-C_6)$alkyl, $(C_1-C_6)$alkoxy, $(C_1-C_6)$alkanoyl, $(C_1-C_6)$alkanoyloxy, or $(C_3-C_6)$cycloalkyl; wherein $R_a$ and $R_b$ are each independently hydrogen, $(C_1-C_6)$alkyl, $(C_1-C_6)$alkanoyl, phenyl, benzyl, or phenethyl;
- W is $-N(R_c)-$;
- Z is $-N(R_d)-$ or $-C(R_e)(R_f)-$;
- $R_c$, $R_d$, $R_e$, and $R_f$ are each independently hydrogen, $(C_1-C_6)$alkyl, $(C_3-C_6)$cycloalkyl, aryl, heteroaryl, aryl$(C_1-C_6)$alkyl, heteroaryl$(C_1-C_6)$alkyl, $(C_1-C_6)$alkanoyl, arylcarbonyl, heteroarylcarbonyl, arylcarbonyl$(C_1-C_6)$alkyl, or heteroarylcarbonyl$(C_1-C_6)$alkyl, wherein any aryl or heteroaryl may optionally be substituted on carbon by 1, 2 or 3 U;
- each U is independently halo, nitro, cyano, hydroxy, trifluoromethyl, trifluoromethoxy, $(C_1-C_6)$alkyl, $(C_3-C_6)$cycloalkyl, $(C_1-C_6)$alkoxy, $(C_1-C_6)$alkanoyl, $(C_2-C_6)$alkanoyloxy, $C(=O)OR_g$, $C(=O)NR_hR_i$, or $NR_jR_k$;
- wherein any $(C_1-C_6)$alkyl, $(C_3-C_6)$cycloalkyl, or $(C_1-C_6)$alkoxy in $R^1$, $R^2$, $R_c$, $R_d$, $R_e$, $R_f$, or U may optionally be substituted on carbon by 1, 2 or 3 V;
- each V is independently halo, nitro, cyano, hydroxy, $(C_3-C_6)$cycloalkyl, $(C_1-C_6)$alkoxy, $(C_1-C_6)$alkanoyl, $(C_2-C_6)$alkanoyloxy, $C(=O)OR_m$, $C(=O)NR_nR_o$, $NR_pR_q$;
- each $R_g$, $R_h$, $R_i$, $R_m$, $R_n$, and $R_o$ is independently hydrogen or $(C_1-C_6)$alkyl; and
- each $R_j$, $R_k$, $R_p$, and $R_q$ is independently hydrogen, $(C_1-C_6)$alkyl, $(C_1-C_6)$alkanoyl, phenyl, benzyl, or phenethyl; or a pharmaceutically acceptable salt thereof.

16. The method of claim 14 or 15 wherein the monoamine is dopamine.

17. The method of claim 14 or 15 wherein the monoamine is serotonin.

18. The method of claim 14 or 15 wherein the monoamine is norepinephrine.

19. The method of claim 15 wherein the disease or condition is pain.

20. The method of claim 15 wherein the disease or condition is headache or migraine.

* * * * *

UNITED STATES PATENT AND TRADEMARK OFFICE
CERTIFICATE OF CORRECTION

PATENT NO.: 5,948,807

DATED: September 7, 1999

INVENTOR(S): Efange et al.

It is certified that error appears in the above-identified patent and that said Letters Patent is hereby corrected as shown below:

In abstract insert --(i.e. serotonin)-- after "monoamine".
In column 16, line 58, delete "($C_1C_6$)" and insert --($C_1$-$C_6$)--, therefor.
In column 16, line 63, delete "($R^a$)" and insert --($R_a$)--, therefor.
In column 17, line 16, delete "$R_a$" and insert --$R_a$--, therefor.
In column 18, line 55, delete "($C_1C_6$)" - and insert --($C_1$-$C_6$)--, therefor.
In column 22, line 62, delete "or".

Signed and Sealed this

Twenty-seventh Day of March, 2001

Attest:

NICHOLAS P. GODICI

Attesting Officer

Acting Director of the United States Patent and Trademark Office